United States Patent
Yang et al.

(10) Patent No.: US 11,097,256 B2
(45) Date of Patent: Aug. 24, 2021

(54) MOLECULAR SIEVE SCM-14, A PREPARATION PROCESS AND USE THEREOF

(71) Applicants: CHINA PETROLEUM & CHEMICAL CORPORATION, Beijing (CN); SHANGHAI RESEARCH INSTITUTE OF PETROCHEMICAL TECHNOLOGY, SINOPEC, Shanghai (CN)

(72) Inventors: Weimin Yang, Shanghai (CN); Zhendong Wang, Shanghai (CN); Yi Luo, Shanghai (CN); Hongmin Sun, Shanghai (CN); Bin Zhang, Shanghai (CN)

(73) Assignees: CHINA PETROLEUM & CHEMICAL CORPORATION, Beijing (CN); SHANGHAI RESEARCH INSTITUTE OF PETROCHEMICAL TECHNOLOGY, SINOPEC, Shanghai (CN)

( * ) Notice: Subject to any disclaimer, the term of this patent is extended or adjusted under 35 U.S.C. 154(b) by 0 days.

(21) Appl. No.: 16/622,806

(22) PCT Filed: Oct. 31, 2017

(86) PCT No.: PCT/CN2017/108461
§ 371 (c)(1),
(2) Date: Dec. 13, 2019

(87) PCT Pub. No.: WO2018/227849
PCT Pub. Date: Dec. 20, 2018

(65) Prior Publication Data
US 2020/0188892 A1    Jun. 18, 2020

(30) Foreign Application Priority Data

Jun. 13, 2017  (CN) .......................... 201710440330.6

(51) Int. Cl.
*C01B 39/48*  (2006.01)
*B01J 20/18*  (2006.01)
(Continued)

(52) U.S. Cl.
CPC ............. *B01J 29/047* (2013.01); *B01J 20/18* (2013.01); *B01J 29/70* (2013.01); *B01J 29/86* (2013.01);
(Continued)

(58) Field of Classification Search
CPC ....... C01B 39/48; C01B 39/06; C01B 37/005; C01B 37/007; B01J 20/18; B01J 29/047;
(Continued)

(56) References Cited

U.S. PATENT DOCUMENTS 2,882,243 A   4/1959   Milton et al.
2,882,244 A   4/1959   Milton
(Continued)

FOREIGN PATENT DOCUMENTS

CN   104445246 A   3/2015
CN   106673009 A   5/2017
(Continued)

OTHER PUBLICATIONS

Michels et al, "Effects of Binders on the Performance of Shaped Hierarchical MFI Zeolites in Methanol-to-Hydrocarbons" ACS Catal. 2014, 4, 8, 2409-2417 (Jun. 2014) (Year: 2014).*
(Continued)

*Primary Examiner* — David M Brunsman
(74) *Attorney, Agent, or Firm* — Novick, Kim & Lee, PLLC; Allen Xue

(57) ABSTRACT

The invention relates to a molecular sieve SCM-14, a preparation process and use thereof. The molecular sieve has
(Continued)

a schematic chemical composition of a formula of "SiO$_2$.1/nGeO$_2$" or a formula of "kF.mQ.SiO$_2$.1/nGeO$_2$.pH$_2$O", wherein the molar ratio of silicon to germanium, n, satisfies n≤30, and other values and symbols are defined in the specification. The molecular sieve has unique XRD diffraction data and can be used as an adsorbent or a catalyst.

16 Claims, 1 Drawing Sheet

(51) Int. Cl.

| | | |
|---|---|---|
| *B01J 29/04* | (2006.01) | |
| *B01J 29/70* | (2006.01) | |
| *C07C 4/18* | (2006.01) | |
| *B01J 29/86* | (2006.01) | |
| *B01J 29/89* | (2006.01) | |
| *B01J 35/10* | (2006.01) | |
| *B01J 37/00* | (2006.01) | |
| *B01J 37/03* | (2006.01) | |
| *B01J 37/04* | (2006.01) | |
| *B01J 37/08* | (2006.01) | |
| *C01B 37/00* | (2006.01) | |
| *C01B 39/06* | (2006.01) | |

(52) U.S. Cl.
CPC ............ *B01J 29/89* (2013.01); *B01J 35/1019* (2013.01); *B01J 35/1038* (2013.01); *B01J 37/0018* (2013.01); *B01J 37/031* (2013.01); *B01J 37/04* (2013.01); *B01J 37/08* (2013.01); *C01B 37/005* (2013.01); *C01B 37/007* (2013.01); *C01B 39/06* (2013.01); *C01B 39/48* (2013.01); *C07C 4/18* (2013.01); *C01P 2002/72* (2013.01); *C01P 2002/74* (2013.01); *C01P 2002/77* (2013.01); *C07C 2529/04* (2013.01)

(58) Field of Classification Search
CPC .. B01J 29/70; C07C 2529/03; C07C 2529/70; C01P 2002/72
See application file for complete search history.

(56) References Cited

U.S. PATENT DOCUMENTS

| | | |
|---|---|---|
| 3,130,007 A | 4/1964 | Breck |
| 3,702,886 A | 11/1972 | Argauer et al. |
| 3,709,979 A | 1/1973 | Chu |
| 3,832,449 A | 8/1974 | Rosinski et al. |
| 4,016,245 A | 4/1977 | Plank et al. |
| 4,076,842 A | 2/1978 | Plank et al. |
| 4,410,501 A | 10/1983 | Taramasso et al. |
| 4,439,409 A | 3/1984 | Puppe et al. |
| 4,954,325 A | 9/1990 | Rubin et al. |
| 5,362,697 A | 11/1994 | Fung et al. |
| 6,162,416 A | 12/2000 | Gajda et al. |
| 2016/0346771 A1 | 12/2016 | Schmidt et al. |
| 2016/0368778 A1 | 12/2016 | Weston et al. |

FOREIGN PATENT DOCUMENTS

| | | | |
|---|---|---|---|
| CN | 106673010 A | 5/2017 | |
| CN | 111099612 A | 5/2020 | |
| EP | 3165280 A1 | 5/2017 | |
| EP | 3165282 A1 | 5/2017 | |
| EP | 3640207 A1 | 4/2020 | |
| JP | 2006313664 A | 11/2006 | |
| JP | 2007161571 A | 6/2007 | |
| JP | 2012512800 A | 6/2012 | |
| WO | 2008035374 A2 | 3/2008 | |
| WO | WO-2017216410 A1 * | 12/2017 | ............. B01D 53/94 |

OTHER PUBLICATIONS

Luo, Yi et al.; Synthesis and Structure Determination of Large-Pore Zeolite SCM-14; Chemistry A European Journal, vol. 23, No. 66, Oct. 2, 2017, pp. 16829-16834, XP055766072.

* cited by examiner

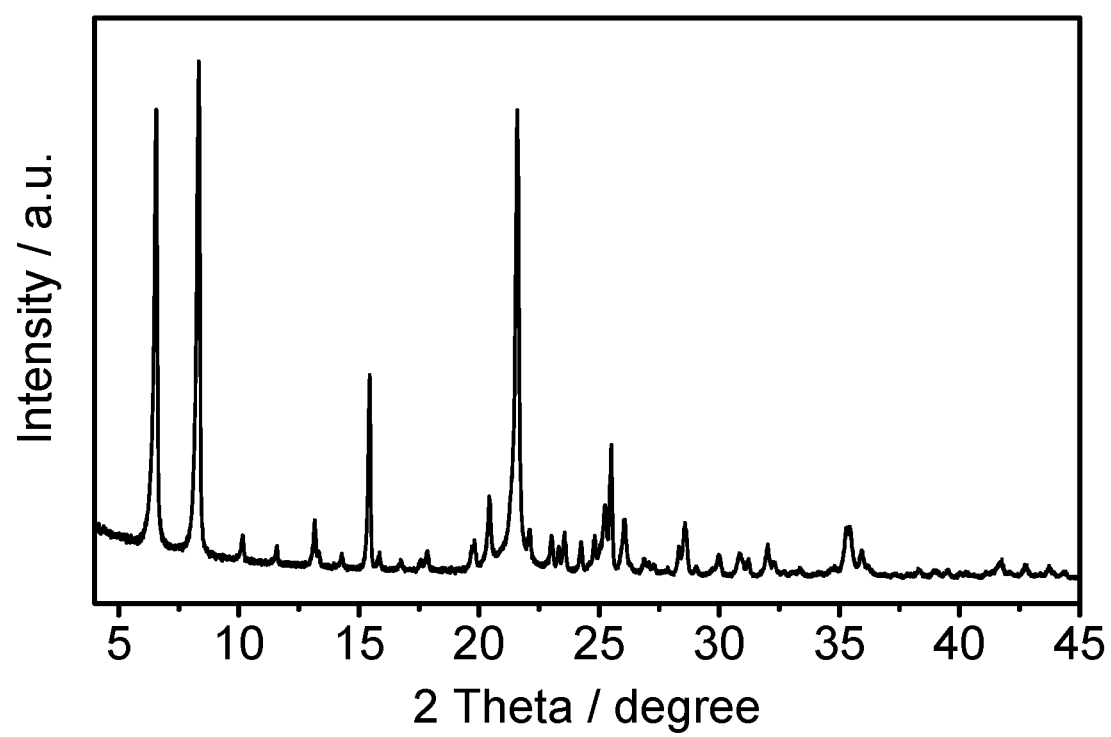

MOLECULAR SIEVE SCM-14, A PREPARATION PROCESS AND USE THEREOF

This application is a 371 national stage filing of PCT/CN2017/108461, filed Oct. 31, 2017.

TECHNICAL FIELD

The invention relates to a molecular sieve SCM-14, a preparation process and use thereof.

BACKGROUND

In industry, porous inorganic materials are widely used as catalysts and catalyst supports. A porous material has a relatively high specific surface and an open channel structure, and is therefore a good catalytic material or catalyst support. The porous material may generally comprise: amorphous porous materials, crystalline molecular sieves, modified layered materials, and the like. The subtle differences in the structures of these materials are indicatives of significant differences in their catalytic and adsorption properties, as well as differences in the various observable properties used to characterize them, such as the morphology, specific surface area, porosity and variability of these dimensions.

The basic skeleton structure of crystalline microporous zeolite is based on a rigid three-dimensional $TO_4$ ($SiO_4$, $AlO_4$, etc.) unit structure; in which structure, $TO_4$ shares oxygen atoms in a tetrahedral structure, and the charge balance of the skeleton tetrahedron, such as $AlO_4$, is maintained through the presence of surface cations such as $Na^+$ and $H^+$. It can be seen that the properties of the zeolite can be altered by cation exchange. At the same time, there exists abundant pores with uniform opening in the structure of a zeolite. These pores are interlaced to form a three-dimensional network structure, and the skeleton can still be stably retained after the removal of the occluded water or organic species (U.S. Pat. No. 4,439,409). Based on the above structure, zeolite not only has good catalytic activity, excellent shape-selection, but also has good selectivity by modification (U.S. Pat. Nos. 6,162,416, 4,954,325, and 5,362,697) in various organic reactions.

The specific structure of a molecular sieve is determined by an X-ray diffraction pattern (XRD), and the X-ray diffraction pattern (XRD) is measured by an X-ray powder diffractometer using a Cu-Kα ray source with a nickel filter. Different zeolite molecular sieves have different XRD patterns. Known molecular sieves, such as zeolite A (U.S. Pat. No. 2,882,243), zeolite Y (U.S. Pat. No. 3,130,007), PSH-3 molecular sieve (U.S. Pat. No. 4,439,409), ZSM-11 molecular sieve (U.S. Pat. No. 3,709,979), ZSM-12 molecular sieve (U.S. Pat. No. 3,832,449), ZSM-23 molecular sieve (U.S. Pat. No. 4,076,842), ZSM-35 molecular sieve (U.S. Pat. No. 4,016,245), MCM-22 molecular sieve (U.S. Pat. No. 4,954,325), etc. each have XRD spectra of their respective characteristics.

At the same time, zeolites with same characteristic XRD spectrum but different types of skeleton atoms will be considered as different molecular sieves. For example, TS-1 molecular sieve (U.S. Pat. No. 4,410,501) and ZSM-5 molecular sieve (U.S. Pat. No. 3,702,886) have the same characteristic XRD patterns, but have different skeleton elements. Specifically, the TS-1 molecular sieve comprises skeleton elements of Si and Ti, exhibiting a catalytic oxidation ability, while the ZSM-5 molecular sieve comprises skeleton elements of Si and Al, exhibiting an acidic catalytic ability.

In addition, molecular sieves with the same characteristic XRD spectrum and the same types of skeleton elements but with different relative amounts of the skeleton elements, will be identified as different molecular sieves as well. For example, X zeolite (U.S. Pat. No. 2,882,244) and Y zeolite (U.S. Pat. No. 3,130,007), share the same characterizing XRD spectrum and the same types of skeleton elements (Si and Al), but with different relative amounts of Si and Al. Specifically, X zeolite has a Si/Al molar ratio of less than 1.5, while Y zeolite has a Si/Al molar ratio of higher than 1.5 spectrum

SUMMARY OF THE INVENTION

The inventors have made deep study on the basis of the prior art and found a novel molecular sieve SCM-14, and further identified beneficial properties thereof.

Specifically, the present invention relates to a molecular sieve SCM-14, characterized in that the molecular sieve has an X-ray diffraction pattern as substantially shown in the table below.

| 2θ (°) [a] | d-distance (Å) | Relative intensity ($I/I_0$ × 100) |
|---|---|---|
| 6.632 | 13.344 + −0.603 | s-vs |
| 8.384 | 10.551 +/− 0.377 | s-vs |
| 15.587 | 5.682 + − 0.109 | w-m |
| 20.661 | 4.296 +/− 0.062 | w |
| 21.692 | 4.094 +/− 0.056 | w-vs |
| 25.693 | 3.465 +/− 0.040 | w-m |

[a] = ±0.3°.

The present invention also provides a process for the preparation of the molecular sieve SCM-14.

TECHNICAL EFFECT

According to the present invention, the SCM-14 molecular sieve involved has a skeleton structure which has never been obtained before in the art.

DESCRIPTION OF DRAWINGS

FIG. 1 is an X-ray diffraction pattern (XRD) of the molecular sieve (in the calcined form) obtained in Example 1.

EMBODIMENTS

The embodiments of the present invention will be illustrated in detail below, while it should be understood that the protection scopes of the present invention are no restricted thereto; instead, the protection scopes are defined by the claims attached.

All publications, patent applications, patents and other references mentioned in this specification are hereby incorporated by reference. Unless otherwise defined, the scientific and technical terms used in the specification have the meanings conventionally known by those skilled in the art. For conflicting meanings of the terms, they shall be understood by the definitions of the present specification.

When the present specification mentions a material, substance, method, step, device, or component, etc. with the derivative words "known to those skilled in the art", "prior art" or the like, the term derived is intended to cover those conventionally used in the field of the present application, but also cover those that are not currently known, whilst will become known in the art to be useful for the similar purposes.

In the context of this specification, the term "specific surface area" refers to the total area of a unit weight of sample, including the internal surface area and the external surface area. Non-porous samples have only external surface areas, such as silicate cement, some clay mineral particles, etc.; while porous samples have both external and internal surface areas, such as asbestos fibers, diatomaceous earth and molecular sieves. The surface area of pores having pore diameters less than 2 nm in a porous sample is the internal surface area, the surface area after deducting the internal surface area from the total surface area is referred to as the external surface area, and the external surface area per unit weight of a sample is the external specific surface area.

In the context of this specification, the term "pore volume" refers to the volume of pores per unit weight of porous material. The term "total pore volume" refers to the volume of all pores (generally only the pores having a pore diameter of less than 50 nm) per unit weight of molecular sieve. The term "micropore volume" refers to the volume of all micropores (generally the pores having a pore diameter of less than 2 nm) per unit weight of molecular sieve.

In the context of the present specification, in the XRD data of a molecular sieve, w, m, s, and vs represent the intensities of the diffraction peaks, wherein w represents weak, m represents medium, s represents strong, and vs represents very strong, which are known to those skilled in the art. In general, w is less than 20; m is 20-40; s is 40-70; and vs is greater than 70.

In the context of the present specification, the structure of a molecular sieve is determined by X-ray diffraction (XRD), wherein the X-ray diffraction pattern (XRD) of the molecular sieve is collected using an X-ray powder diffractometer equipped with a Cu-Kα ray source, with Kα1 wavelength λ=1.5405980 angstroms (Å) and a nickel filter.

In the context of the present specification, the so-called prepared state, prepared form or prepared molecular sieve refers to the state of the molecular sieve after the completion of the preparation. As the prepared state, a specific example may be the state directly presented after completion of the preparation (generally called as a precursor of molecular sieve). Thus, in the prepared state, the molecular sieve may contain water and/or may contain organic substances (in particular organic template).

In the context of this specification, the term "calcined", "calcined form" or "calcined molecular sieve" refers to the state of the molecular sieve after calcination. As the state after calcination, for example, may be a state obtained by further removing organic substances (particularly, organic templating agents) and water, etc. that may be present in the pores of the prepared molecular sieve by calcination. Here, the conditions of the calcination include, in particular: calcinating at 550° C. for 6 hours in an air atmosphere.

It should be particularly understood that two or more of the aspects (or embodiments) disclosed in the context of this specification can be combined with each other as desired, and that such combined embodiments (e.g., methods or systems) are incorporated herein and constitute a part of this original disclosure, while remaining within the scope of the present invention.

Without otherwise specifically indicated, all percentages, parts, ratios, etc. mentioned in this specification are provided by weight, unless the basis by weight is not in accordance with the conventional knowledge of those skilled in the art.

According to an aspect of the present invention, the invention relates to molecular sieve SCM-14. The molecular sieve, particularly in its prepared form or calcined form, has an X-ray diffraction pattern substantially as shown in Table A-1 or Table A-2 below.

TABLE A-1

| 2 θ (°) [a] | d-distance (Å) [b] | Relative intensity ($I/I_0 \times 100$) |
|---|---|---|
| 6.632 | 13.317 | s-vs |
| 8.384 | 10.537 | s-vs |
| 15.587 | 5.680 | w-m |
| 20.661 | 4.295 | w |
| 21.692 | 4.094 | w-vs |
| 25.693 | 3.464 | w-m |

[a] = ±0.3°,
[b] is a function of 2 θ.

TABLE A-2

| 2 θ (°) [a] | d-distance (Å) | Relative intensity ($I/I_0 \times 100$) |
|---|---|---|
| 6.632 | 13.344 +/− 0.603 | s-vs |
| 8.384 | 10.551 +/− 0.377 | s-vs |
| 15.587 | 5.682 +/− 0.109 | w-m |
| 20.661 | 4.296 +/− 0.062 | w |
| 21.692 | 4.094 +/− 0.056 | w-vs |
| 25.693 | 3.465 +/− 0.040 | w-m |

[a] = ±0.3°.

According to an aspect of the present invention, the X-ray diffraction pattern may further comprise X-ray diffraction peaks substantially as shown in Table B-1 or Table B-2 below.

TABLE B-1

| 2 θ (°) [a] | d-distance (Å) [b] | Relative intensity ($I/I_0 \times 100$) |
|---|---|---|
| 10.289 | 8.591 | w |
| 11.677 | 7.572 | w |
| 13.287 | 6.658 | w |
| 26.231 | 3.395 | w |

[a] = ±0.3°,
[b] is a function of 2 θ.

TABLE B-2

| 2θ (°)[a] | d-distance (Å) [b] | Relative intensity ($I/I_0 \times 100$) |
|---|---|---|
| 10.289 | 8.598 ± 0.250 | w |
| 11.677 | 7.577 ± 0.194 | w |
| 13.287 | 6.661 ± 0.150 | w |
| 26.231 | 3.395 ± 0.038 | w |

[a] = ±0.3°.

According to an aspect of the present invention, the X-ray diffraction pattern optionally further comprises X-ray diffraction peaks substantially as shown in the following Table.

| 2θ (°)[a] | d-distance (Å) [b] | Relative intensity ($I/I_0 \times 100$) |
|---|---|---|
| 14.397 | 6.150 ± 0.127 | w |
| 23.479 | 3.786 ± 0.048 | w |

| 2θ (°)[a] | d-distance (Å) [b] | Relative intensity ($I/I_0 \times 100$) |
|---|---|---|
| 23.798 | 3.736 ± 0.046 | w |
| 24.421 | 3.642 ± 0.044 | w |

[a] = ±0.3°.

According to an aspect of the present invention, the molecular sieve SCM-14 has a schematic chemical composition I as shown with the formula "$SiO_2 \cdot 1/nGeO_2$". It is known that molecular sieves sometimes contain a certain amount of moisture, particularly immediately after preparation, but it is not considered necessary to specify the amount of the moisture in the present invention because the presence or absence of this moisture does not substantially affect the XRD spectrum of the molecular sieve. In view of this, the schematic chemical composition represents in fact the anhydrous chemical composition of the molecular sieve. Moreover, it is apparent that the schematic chemical composition I represents the framework chemical composition of the SCM-14 molecular sieve.

According to an aspect of the present invention, in the schematic chemical composition I, the molar ratio of silicon to germanium, n, satisfies n≤30, preferably 0.5≤n≤20, more preferably 1≤n≤10, more preferably 1≤n≤5.

According to an aspect of the present invention, the molecular sieve may further generally contain organic species (particularly organic template) and water, etc. in composition, such as those filling the pores thereof, immediately after preparation. Thus, the molecular sieve SCM-14 may also have a schematic chemical composition II shown with the formula "$kF \cdot mQ \cdot SiO_2 \cdot 1/nGeO_2 \cdot pH_2O$". Here, the molecular sieve having the schematic chemical composition I can be obtained by calcining the molecular sieve having the schematic chemical composition II (sometimes called as a molecular sieve precursor) to remove any organic template, water, and the like present in the pores thereof. In addition, the calcination may be carried out in any manner conventionally known in the art. For example, the calcination temperature is generally from 300° C. to 750° C., preferably from 400° C. to 600° C., and the calcination duration is generally from 1 hour to 10 hours, preferably from 3 hours to 6 hours. In addition, the calcination is generally carried out in an oxygen-containing atmosphere, such as in air or oxygen atmosphere. In this regard, the schematic chemical composition I is sometimes also referred to as a post-firing schematic chemical composition, and the schematic chemical composition II is sometimes also referred to as a prepared form schematic chemical composition.

According to an aspect of the present invention, in the schematic chemical composition II, the molar ratio of silicon to germanium, n, satisfies n≤30, preferably 0.5≤n≤20, more preferably 1≤n≤10, more preferably 1≤n≤5.

According to an aspect of the present invention, in the schematic chemical composition II, F is fluorine, and 0.005≤k≤0.8, preferably 0.01≤k≤0.6, more preferably 0.01≤k≤0.4, more preferably 0.02≤k≤0.2.

According to an aspect of the present invention, in the schematic chemical composition II, Q is an organic Template agent, 0.005≤m≤1.0, preferably 0.01≤m≤0.6, more preferably 0.02≤m≤0.3, or more preferably 0.04≤m≤0.1. According to an aspect of the present invention, in the schematic chemical composition II, the organic Template agent is selected from 4-pyrrolidinylpyridine, or a quaternary ammonium form represented by formula (A-1), formula (A-2), or formula (A-3), preferably 4-pyrrolidinylpyridine. These organic Template agents may be used alone or as a combination in a desired ratio.

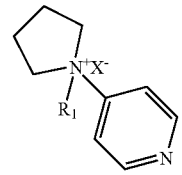

(A-1)

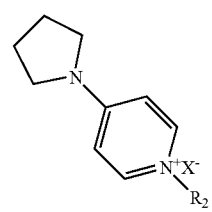

(A-2)

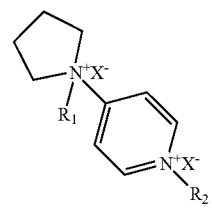

(A-3)

In each formula, $R_1$ and $R_2$ are each independently H or $C_{1-8}$ alkyl, preferably $C_{1-4}$ alkyl, more preferably $C_{1-2}$ alkyl, and $X^-$ are each independently a halogen ion (such as $Cl^-$, $Br^-$, and $I^-$) and a hydroxide ion ($OH^-$), preferably hydroxide ion ($OH^-$).

According to an aspect of the present invention, in the schematic chemical composition II, 0.005≤p≤0.5, preferably 0.01≤p≤0.4, more preferably 0.01≤p≤0.3, more preferably 0.02≤p≤0.2.

According to an aspect of the present invention, in the molecular sieve SCM-14, germanium on the framework may be partially replaced by a trivalent or tetravalent element other than silicon and germanium, with a replacement ratio not exceeding 10%. Here, the parameter "replacement ratio" is dimensionless. The element other than silicon and germanium is at least one selected from the group consisting of boron, aluminum, tin, zirconium and titanium, preferably at least one selected from the group consisting of boron and titanium. When germanium is replaced by a trivalent element, such as boron or aluminum, the replacement ratio=$2X_2O_3/(2X_2O_3+GeO_2) \times 100\%$, wherein X is a trivalent element. When germanium is replaced by a tetravalent element, such as tin, zirconium, or titanium, the replacement ratio=$YO_2/(YO_2+GeO_2) \times 100\%$, wherein Y is a tetravalent element. In calculating the replacement ratio, the moles of the corresponding oxide are used.

According to an aspect of the present invention, the molecular sieve SCM-14 has a specific surface area (according to BET method) of 100-500 $m^2/g$, preferably 130-300 $m^2/g$.

According to an aspect of the present invention, the molecular sieve SCM-14 has a micropore volume (according to t-plot method) of 0.04 to 0.2 $cm^3/g$, preferably 0.05 to 0.16 $cm^3/g$.

According to an aspect of the present invention, the molecular sieve SCM-14 can be prepared by the following processes. In view of this, the present invention also relates to a process of preparing a molecular sieve SCM-14, comprising the step of: crystallizing a mixture (hereinafter called as mixture) comprising or formed from a silicon source, a germanium source, a fluorine source, an organic template and water, to obtain said molecular sieve.

According to an aspect of the present invention, in the process of preparing the molecular sieve, the organic template is selected from 4-pyrrolidinyl pyridine, or a quaternary ammonium form represented by formula (A-1), formula (A-2) or formula (A-3), preferably 4-pyrrolidinyl pyridine. The organic Template agents may be used alone or as a combination in a desired ratio.

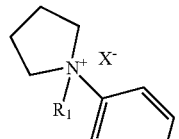
(A-1)

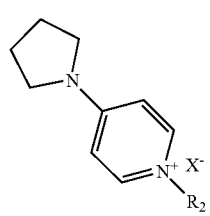
(A-2)

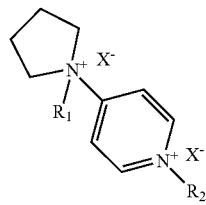
(A-3)

In each formula, $R_1$ and $R_2$ are each independently H or $C_{1-8}$ alkyl, preferably $C_{1-4}$ alkyl, more preferably $C_{1-2}$ alkyl, and $X^-$ are each independently a halogen ion (such as $Cl^-$, $Br^-$, and $I^-$) and a hydroxide ion ($OH^-$), preferably hydroxide ion ($OH^-$).

According to an aspect of the present invention, in the process of preparing the molecular sieve, the crystallization step may be performed in any manner conventionally known in the art, such as a method of mixing the silicon source, the germanium source, the fluorine source, the organic template and water in a given ratio, and hydrothermally crystallizing the obtained mixture under the crystallization conditions. Stirring may be applied as required.

According to an aspect of the present invention, in the process of preparing the molecular sieve, any silicon source conventionally used in the art for this purpose may be used as the silicon source. Examples thereof include silicic acid, silica gel, silica sol, tetraalkyl orthosilicate, and water glass. These silicon sources may be used alone or as a combination in a desired ratio.

According to an aspect of the present invention, in the process of preparing the molecular sieve, any germanium source conventionally used in the art for this purpose may be used as the germanium source, including but not limited to germanium oxide, germanium nitrate, and tetraalkoxy germanium.

According to an aspect of the present invention, in the process of preparing the molecular sieve, any fluorine source conventionally used for this purpose in the art may be used as the fluorine source, and examples thereof include fluoride or an aqueous solution thereof, particularly hydrofluoric acid and the like.

According to an aspect of the present invention, in the process of preparing the molecular sieve, the molar ratio of the silicon source (calculated as $SiO_2$), the germanium source (calculated as $GeO_2$), the fluorine source (calculated as F), the organic template and water is generally from 1:(1/30-∞): (0.1-1.0): (0.1-1.0): (5-50); preferably 1:(0.05-2): (0.1-0.8): (0.1-0.8): (10-40); more preferably 1:(0.1-1): (0.2-0.6): (0.2-0.6): (15-30); or more preferably 1:(0.2-1): (0.3-0.5): (0.3-0.5): (15-20).

According to an aspect of the present invention, in the process of preparing the molecular sieve, the crystallization conditions include: firstly, crystallizing at 91-130° C. for 8 hours to 3 days, and then crystallizing at 140-210° C. for 1-15 days; preferably, crystallizing firstly at 100-130° C. for 12 hours to 2 days, and then crystallizing at 150-190° C. for 2 to 10 days; more preferably, crystallizing firstly at 100-120° C. for 12 to 36 hours and then crystallizing at 160-180° C. for 2 to 7 days.

According to an aspect of the present invention, in the process of preparing the molecular sieve, an ageing step before crystallization is included, and the ageing conditions include: an ageing temperature of 50-90° C., and an ageing duration of 30 minutes to 2 days.

According to an aspect of the present invention, in the process of preparing the molecular sieve, when germanium atoms are replaced with trivalent or tetravalent elements other than silicon and germanium, a source of the trivalent or tetravalent elements other than silicon and germanium, preferably a source of oxide of the trivalent or tetravalent elements other than silicon and germanium, is added to the mixture. As the source of oxide, at least one selected from the group consisting of a boron oxide source, an aluminum oxide source, a tin oxide source, a zirconium oxide source, and a titanium oxide source is preferable. Specific examples of the aluminum oxide source include at least one selected from the group consisting of aluminum hydroxide, sodium aluminate, aluminum salt, kaolin and montmorillonite. Specific examples of the boron oxide source include at least one selected from the group consisting of boron oxide, borax, sodium metaborate, and boric acid. Specific examples of the tin oxide source include at least one selected from the group consisting of tin tetrachloride, stannous chloride, alkyl tin, alkoxy tin, and organic stannates. Specific examples of the zirconia source include at least one selected from the group consisting of zirconium salts (e.g., zirconium nitrate or zirconium sulfate), alkyl zirconium, alkoxy zirconium, and organic zirconates. Specific examples of the titanium oxide source include one or more selected from tetraalkyl titanates (e.g., tetramethyl titanate, tetraethyl titanate, tetrapropyl titanate, tetra-n-butyl titanate), $TiCl_4$, hexafluorotitanic acid, $Ti(SO_4)_2$, and hydrolysis products thereof.

According to an aspect of the present invention, in the process of preparing the molecular sieve, the molar ratio of the oxide source (calculated as the corresponding oxide) to the germanium source (calculated as $GeO_2$) when used is generally (0.01-0.1): 1, preferably (0.02-0.08): 1.

According to an aspect of the present invention, in the process of preparing the molecular sieve, after the crystallization is completed, the molecular sieve can be separated as a product from the obtained reaction mixture by any separation methods conventionally known, thereby obtaining the molecular sieve SCM-14, which is also called as prepared form of molecular sieve SCM-14. The separation method includes, for example, a method of filtering, washing and drying the obtained reaction mixture.

According to an aspect of the present invention, in the process of preparing the molecular sieve, the filtering, washing and drying may be performed by any method conventionally known in the art. Specifically, for example, the reaction mixture obtained may be simply filtered by suction. Examples of the washing include washing with deionized water. The drying temperature is, for example, 40 to 250° C., preferably 60 to 150° C., and the drying duration is, for example, 8 to 30 hours, preferably 10 to 20 hours. The drying may be carried out under normal pressure or under reduced pressure.

According to an aspect of the present invention, in the process of preparing the molecular sieve, the molecular sieve obtained by crystallization may be calcined, as needed, to remove the organic template and if any, the water, etc., and thus to obtain the calcined molecular sieve, which is also called as calcined form of molecular sieve SCM-14. The calcination may be carried out in any manner conventionally known in the art, for example, the calcination temperature is generally 300 to 800° C., preferably 400 to 650° C., and the calcination duration is generally 1 to 10 hours, preferably 3 to 6 hours. In addition, the calcination is generally carried out in an oxygen-containing atmosphere, such as air or oxygen atmosphere.

According to an aspect of the present invention, the molecular sieve SCM-14 may be in any physical form, such as a powder, granule, or molded article (e.g., a bar, clover, etc.). These physical forms can be obtained in any manner conventionally known in the art and are not particularly limited.

According to an aspect of the present invention, the molecular sieve SCM-14 may be used in combination with other materials, thereby obtaining a molecular sieve composition. Examples of the other materials include active materials and inactive materials. Examples of the active material include synthetic zeolite and natural zeolite, and examples of the inactive material (generally called as a binder) include clay, carclazyte, and alumina. These other materials may be used alone or as a combination in any ratio. The amounts of the other materials can refer to those conventionally used in the art, without particular limitation.

According to an aspect of the present invention, the molecular sieve SCM-14 or the molecular sieve composition may be used as an adsorbent, for example to separate at least one component from a mixture of a plurality of components in the gas or liquid phase. Thus, at least one component may be partially or substantially completely separated from the mixture of the plurality of components by contacting the mixture with said molecular sieve SCM-14 or said molecular sieve composition, so as to selectively adsorb such a component.

According to an aspect of the present invention, the molecular sieve SCM-14 or the molecular sieve composition may also be used as a catalyst (or as a catalytically active component thereof) either directly or after having been subjected to necessary treatments or conversions (such as ion exchange, etc.) conventionally performed in the art for molecular sieves. To this end, according to an aspect of the present invention, it is possible, for example, to subject a reactant (such as a hydrocarbon) to a given reaction in the presence of the catalyst, and thereby obtain a target product.

EXAMPLES

The present invention will be described in further detail with reference to examples, whilst the present invention is not limited to these examples.

Example 1

10.08 g of deionized water, 3.045 g of organic template agent of 4-pyrrolidinylpyridine (98 wt %), 1.674 g of germanium oxide (99 wt %), 1.0 g of hydrofluoric acid (40 wt %) and 6.0 g of silica sol ($SiO_2$ 40 wt %) were uniformly mixed to obtain a reaction mixture, wherein the material ratios (molar ratios) of the reaction mixture were as follows:

$SiO_2/GeO_2$=2.5
Template agent/$SiO_2$=0.50
F/$SiO_2$=0.50
$H_2O/SiO_2$=20.

After being mixed uniformly, the mixture was loaded into a stainless steel reactor for aging in a 80° C. water bath for 4 hr, then crystallizing at 100° C. for 2 days under stirring, and further crystallizing at 170° C. for 5 days. After crystallization, the solution was filtered, washed and dried at 150° C. for 8 hours to obtain a molecular sieve precursor with a schematic chemical composition of $0.21F.0.06.Q.SiO_2.1/3.7GeO_2.0.02H_2O$. The precursor was calcined in air at 550° C. for 6 hours to obtain the molecular sieve.

The XRD spectrum data of the product molecular sieve (in a calcined form) was shown in Table 1, and the XRD spectrum was shown in FIG. 1.

The obtained product molecular sieve had a specific surface area of 193 m$^2$/g, and a micropore volume of 0.07 cm$^3$/g.

The product molecular sieve was measured by inductively coupled plasma atomic emission spectroscopy (ICP) to have a $SiO_2/GeO_2$=3.7.

TABLE 1

| 2θ/° | d/Å | $I/I_0 \times 100$ |
|---|---|---|
| 6.553 | 13.4766 | 100 |
| 8.331 | 10.6048 | 72.6 |
| 10.148 | 8.7095 | 5.5 |
| 11.644 | 7.5934 | 2.2 |
| 13.203 | 6.7004 | 8.7 |
| 14.357 | 6.1642 | 2 |
| 15.526 | 5.7027 | 28.1 |
| 17.935 | 4.9417 | 3.2 |
| 19.827 | 4.4742 | 3.2 |
| 20.519 | 4.3247 | 9 |
| 21.759 | 4.081 | 54.3 |
| 23.141 | 3.8404 | 5.3 |
| 23.479 | 3.786 | 0.5 |
| 23.798 | 3.736 | 0.5 |
| 24.398 | 3.6453 | 4.6 |
| 25.681 | 3.466 | 16.5 |
| 26.218 | 3.3963 | 4.4 |
| 27.184 | 3.2776 | 2.5 |
| 28.8 | 3.0973 | 9.5 |
| 30.221 | 2.9549 | 1.7 |
| 31.164 | 2.8675 | 3.4 |
| 32.248 | 2.7736 | 3.8 |
| 35.624 | 2.5182 | 7.6 |
| 46.905 | 1.9354 | 2.4 |

Example 2

Example 1 was repeated, except that the reaction mixture was prepared in the following ratios (molar ratio):
$SiO_2/GeO_2=3$
Template agent/$SiO_2=0.30$
$F/SiO_2=0.30$
$H_2O/SiO_2=18$.

After being mixed uniformly, the mixture was loaded into a stainless steel reactor for aging in a 80° C. water bath for 1 hr, crystallizing at 110° C. for 1 day under stirring, and further crystallizing at 165° C. for 4 days.

The XRD spectrum data of the product (in a calcined form) was shown in Table 2, and the XRD spectrum was similar to that of FIG. 1.

The obtained product molecular sieve had a specific surface area of 190 m$^2$/g, and a micropore volume of 0.07 cm$^3$/g.

The product molecular sieve was measured by inductively coupled plasma atomic emission spectroscopy (ICP) to have a $SiO_2/GeO_2=3.5$.

TABLE 2

| 2θ/° | d/Å | I/I0 × 100 |
|---|---|---|
| 6.553 | 13.4766 | 100 |
| 8.331 | 10.6048 | 72.6 |
| 10.148 | 8.7095 | 5.5 |
| 11.644 | 7.5934 | 2.2 |
| 13.203 | 6.7004 | 8.7 |
| 14.357 | 6.1642 | 2 |
| 15.526 | 5.7027 | 28.1 |
| 17.935 | 4.9417 | 3.2 |
| 19.939 | 4.4493 | 3.2 |
| 20.519 | 4.3247 | 9 |
| 21.759 | 4.081 | 54.3 |
| 23.141 | 3.8404 | 5.3 |
| 23.466 | 3.788 | 0.5 |
| 23.790 | 3.737 | 0.4 |
| 24.398 | 3.6453 | 4.6 |
| 25.03 | 3.5547 | 5.9 |
| 25.628 | 3.473 | 14.4 |
| 26.288 | 3.3874 | 3.3 |
| 27.184 | 3.2776 | 2.5 |
| 28.8 | 3.0973 | 9.5 |
| 31.164 | 2.8675 | 3.4 |
| 32.248 | 2.7736 | 3.8 |
| 35.624 | 2.5182 | 7.6 |
| 42.072 | 2.1459 | 1.7 |
| 46.905 | 1.9354 | 2.4 |

Example 3

Example 1 was repeated, except that the reaction mixture was prepared in the following ratios (molar ratio):
$SiO_2/GeO_2=4$
Template agent/$SiO_2=0.40$
$F/SiO_2=0.40$
$H_2O/SiO_2=15$.

After being mixed uniformly, the mixture was loaded into a stainless steel reactor for crystallizing for 1 day at 110° C. under stirring, and then crystallizing for 7 days at 170° C. under stirring.

The XRD spectrum data of the product (in a calcined form) was shown in Table 3, and the XRD spectrum was similar to that of FIG. 1.

The obtained product molecular sieve had a specific surface area of 210 m$^2$/g, and a micropore volume of 0.08 cm$^3$/g.

The product molecular sieve was measured by inductively coupled plasma atomic emission spectroscopy (ICP) to have a $SiO_2/GeO_2=4.2$.

TABLE 3

| 2θ/° | d/Å | I/I0 × 100 |
|---|---|---|
| 6.576 | 13.4293 | 46.8 |
| 8.278 | 10.6724 | 100 |
| 9.956 | 8.8774 | 1.4 |
| 10.27 | 8.6066 | 4.8 |
| 11.639 | 7.5965 | 1 |
| 13.192 | 6.7058 | 6.5 |
| 13.465 | 6.5702 | 9.4 |
| 14.287 | 6.1943 | 1.3 |
| 15.549 | 5.6943 | 21.6 |
| 15.996 | 5.536 | 1.8 |
| 16.61 | 5.3327 | 0.5 |
| 17.848 | 4.9657 | 8.1 |
| 19.848 | 4.4696 | 7 |
| 20.636 | 4.3006 | 9.4 |
| 21.458 | 4.1376 | 86.5 |
| 22.272 | 3.9883 | 5.2 |
| 23.101 | 3.8469 | 5.2 |
| 23.417 | 3.7958 | 1.6 |
| 23.765 | 3.7409 | 6.4 |
| 24.355 | 3.6516 | 6.1 |
| 25.06 | 3.5504 | 17.8 |
| 25.633 | 3.4724 | 14.5 |
| 26.04 | 3.4191 | 7.3 |
| 27.027 | 3.2964 | 2 |
| 27.734 | 3.214 | 1.2 |
| 28.488 | 3.1305 | 4.2 |
| 28.779 | 3.0996 | 8.3 |
| 29.152 | 3.0608 | 0.9 |
| 29.791 | 2.9965 | 4.1 |
| 30.904 | 2.8911 | 1.2 |
| 31.178 | 2.8664 | 3.7 |
| 31.418 | 2.8449 | 2.9 |
| 31.999 | 2.7946 | 4.3 |
| 32.68 | 2.738 | 1.9 |
| 33.403 | 2.6803 | 1.1 |
| 34.547 | 2.5942 | 1.7 |
| 34.796 | 2.5761 | 2.4 |
| 35.328 | 2.5386 | 7.3 |
| 36.141 | 2.4833 | 2.6 |
| 37.503 | 2.3962 | 0.8 |
| 38.232 | 2.3521 | 1.2 |
| 39.461 | 2.2816 | 1.7 |
| 40.331 | 2.2344 | 1.5 |
| 41.371 | 2.1806 | 2.6 |
| 41.603 | 2.169 | 2.7 |
| 42.391 | 2.1305 | 1.4 |
| 43.005 | 2.1015 | 0.9 |
| 44.101 | 2.0518 | 1.9 |
| 44.608 | 2.0296 | 1.1 |

Example 4

Example 1 was repeated, except that the reaction mixture was prepared in the following ratios (molar ratio):
$SiO_2/GeO_2=2$
Template agent/$SiO_2=0.50$
$F/SiO_2=0.50$
$H_2O/SiO_2=15$.

After being mixed uniformly, the mixture was loaded into a stainless steel reactor for crystallizing for 1 day at 110° C. under stirring, and then crystallizing for 7 days at 150° C. under stirring.

The XRD spectrum data of the product (in a calcined form) was shown in Table 4, and the XRD spectrum was similar to that of FIG. 1.

The obtained product molecular sieve had a specific surface area of 227 m$^2$/g, and a micropore volume of 0.09 cm$^3$/g.

The product molecular sieve was measured by inductively coupled plasma atomic emission spectroscopy (ICP) to have a $SiO_2/GeO_2=2.7$.

TABLE 4

| 2θ/° | d/Å | $I/I_0 \times 100$ |
| --- | --- | --- |
| 6.651 | 13.278 | 100 |
| 8.273 | 10.6793 | 47.9 |
| 10.049 | 8.7952 | 8.7 |
| 10.378 | 8.5166 | 10.1 |
| 13.535 | 6.5364 | 9.2 |
| 14.398 | 6.147 | 0.4 |
| 15.67 | 5.6505 | 23.5 |
| 18.01 | 4.9213 | 9.2 |
| 20.008 | 4.4342 | 11.4 |
| 20.832 | 4.2605 | 10.2 |
| 21.662 | 4.0991 | 33.9 |
| 22.472 | 3.9532 | 6.5 |
| 23.477 | 3.786 | 0.5 |
| 23.789 | 3.737 | 0.4 |
| 24.006 | 3.7039 | 8.6 |
| 24.421 | 3.642 | 0.5 |
| 25.09 | 3.5462 | 8.1 |
| 25.628 | 3.473 | 14.4 |
| 26.218 | 3.3963 | 4.4 |
| 28.743 | 3.1033 | 6.3 |
| 29.039 | 3.0724 | 12.1 |
| 31.477 | 2.8398 | 3.7 |
| 35.624 | 2.5181 | 8.4 |
| 46.985 | 1.9323 | 4.2 |

Example 5

Example 1 was repeated, except that the reaction mixture was prepared in the following ratios (molar ratio):
$SiO_2/GeO_2=3$
Template agent/$SiO_2=0.35$
$F/SiO_2=0.35$
$H_2O/SiO_2=15$.

After being mixed uniformly, the mixture was loaded into a stainless steel reactor for crystallizing for 1 day at 110° C. under stirring, and then crystallizing for 8 days at 150° C. under stirring.

The XRD spectrum data of the product (in a calcined form) was shown in Table 5, and the XRD spectrum was similar to that of FIG. 1.

The obtained product molecular sieve had a specific surface area of 236 m²/g, and a micropore volume of 0.09 cm³/g.

The product molecular sieve was measured by inductively coupled plasma atomic emission spectroscopy (ICP) to have a $SiO_2/GeO_2=3.6$.

TABLE 5

| 2θ/° | d/Å | $I/I_0 \times 100$ |
| --- | --- | --- |
| 6.553 | 13.4766 | 100 |
| 8.331 | 10.6048 | 72.6 |
| 10.148 | 8.7095 | 5.5 |
| 11.644 | 7.5934 | 2.2 |
| 13.203 | 6.7004 | 8.7 |
| 14.357 | 6.1642 | 2 |
| 15.526 | 5.7027 | 28.1 |
| 17.935 | 4.9417 | 3.2 |
| 19.827 | 4.4742 | 3.2 |
| 20.519 | 4.3247 | 9 |
| 21.759 | 4.081 | 54.3 |
| 23.141 | 3.8404 | 5.3 |
| 23.481 | 3.786 | 0.4 |
| 23.805 | 3.735 | 0.5 |

TABLE 5-continued

| 2θ/° | d/Å | $I/I_0 \times 100$ |
| --- | --- | --- |
| 24.398 | 3.6453 | 4.6 |
| 25.681 | 3.466 | 16.5 |
| 26.218 | 3.3963 | 4.4 |
| 27.184 | 3.2776 | 2.5 |
| 28.8 | 3.0973 | 9.5 |
| 30.221 | 2.9549 | 1.7 |
| 31.164 | 2.8675 | 3.4 |
| 32.248 | 2.7736 | 3.8 |
| 35.624 | 2.5182 | 7.6 |
| 46.905 | 1.9354 | 2.4 |

Example 6

Example 1 was repeated, except that tetraethyl silicate was used as a silicon source. After being mixed uniformly, the mixture was placed in a water bath at 80° C. for 3 hours, and then the mixture was placed in a stainless steel reactor and crystallized at 110° C. for 1 day under stirring, and further crystallized at 170° C. for 4 days.

The XRD spectrum data of the product (in a calcined form) was shown in Table 6, and the XRD spectrum was similar to that of FIG. 1.

The obtained product molecular sieve had a specific surface area of 201 m²/g, and a micropore volume of 0.08 cm³/g.

The product molecular sieve was measured by inductively coupled plasma atomic emission spectroscopy (ICP) to have a $SiO_2/GeO_2=3.5$.

TABLE 6

| 2θ/° | d/Å | $I/I_0 \times 100$ |
| --- | --- | --- |
| 6.56 | 13.4633 | 88.7 |
| 8.336 | 10.5982 | 100 |
| 10.17 | 8.6909 | 5.1 |
| 11.582 | 7.6338 | 3.7 |
| 13.166 | 6.7188 | 9.3 |
| 14.288 | 6.1936 | 2.8 |
| 15.449 | 5.7309 | 39.5 |
| 15.855 | 5.5849 | 3.5 |
| 16.736 | 5.2928 | 2.1 |
| 17.574 | 5.0424 | 2.2 |
| 17.864 | 4.9613 | 4 |
| 19.814 | 4.477 | 5.1 |
| 20.43 | 4.3435 | 12.6 |
| 21.599 | 4.1109 | 91.8 |
| 23.02 | 3.8604 | 6.3 |
| 23.318 | 3.8116 | 4.3 |
| 23.567 | 3.772 | 7.5 |
| 24.263 | 3.6653 | 5.7 |
| 24.82 | 3.5843 | 6.8 |
| 25.243 | 3.5251 | 12.8 |
| 25.516 | 3.488 | 25.3 |
| 26.056 | 3.4169 | 10.1 |
| 26.87 | 3.3153 | 2.7 |
| 27.3 | 3.264 | 1.5 |
| 27.858 | 3.2 | 1.2 |
| 28.323 | 3.1484 | 5.5 |
| 28.571 | 3.1216 | 10.4 |
| 29.054 | 3.0709 | 1.6 |
| 29.974 | 2.9787 | 4.1 |
| 30.837 | 2.8972 | 4.5 |
| 31.219 | 2.8626 | 3.4 |
| 32.024 | 2.7925 | 6.4 |
| 32.323 | 2.7674 | 2.6 |
| 32.726 | 2.7342 | 0.7 |
| 33.071 | 2.7064 | 0.8 |
| 33.376 | 2.6824 | 1.5 |
| 34.806 | 2.5754 | 1.3 |

Example 7

Example 1 was repeated, except that boric acid was added into the system as a boron source to replace a part of the germanium source, with a replacement ratio of 1%.

The XRD spectrum data of the product (in a calcined form) was shown in Table 7, and the XRD spectrum was similar to that of FIG. 1.

The obtained product molecular sieve had a specific surface area of 221 m$^2$/g, and a micropore volume of 0.08 cm$^3$/g.

The product molecular sieve was measured by inductively coupled plasma atomic emission spectroscopy (ICP) to have a $SiO_2/GeO_2$=3.7 and a $SiO_2/B_2O_3$=475.2.

TABLE 7

| 2θ/° | d/Å | I/I$_0$ × 100 |
|---|---|---|
| 6.576 | 13.4293 | 46.8 |
| 8.278 | 10.6724 | 100.0 |
| 9.956 | 8.8774 | 1.4 |
| 10.270 | 8.6066 | 4.8 |
| 11.639 | 7.5965 | 1.0 |
| 13.216 | 6.6936 | 6.9 |
| 13.465 | 6.5702 | 9.4 |
| 14.287 | 6.1943 | 1.3 |
| 15.549 | 5.6943 | 21.6 |
| 15.996 | 5.5360 | 1.8 |
| 16.643 | 5.3224 | 0.5 |
| 17.657 | 5.0189 | 4.1 |
| 17.848 | 4.9657 | 8.1 |
| 19.848 | 4.4696 | 7.0 |
| 20.636 | 4.3006 | 9.4 |
| 21.458 | 4.1376 | 86.5 |
| 22.272 | 3.9883 | 5.2 |
| 23.101 | 3.8469 | 5.2 |
| 23.417 | 3.7958 | 1.6 |
| 23.765 | 3.7409 | 6.4 |
| 24.355 | 3.6516 | 6.1 |
| 24.886 | 3.5749 | 9.5 |
| 25.060 | 3.5504 | 17.8 |
| 25.633 | 3.4724 | 14.5 |
| 26.040 | 3.4191 | 7.3 |
| 26.986 | 3.3013 | 2.4 |
| 27.734 | 3.2140 | 1.2 |
| 28.488 | 3.1305 | 4.2 |
| 28.779 | 3.0996 | 8.3 |
| 29.152 | 3.0608 | 0.9 |
| 29.791 | 2.9965 | 4.1 |
| 30.904 | 2.8911 | 1.2 |
| 31.178 | 2.8664 | 3.7 |
| 31.418 | 2.8449 | 2.9 |
| 31.999 | 2.7946 | 4.3 |
| 32.299 | 2.7694 | 1.7 |
| 32.680 | 2.7380 | 1.9 |
| 33.403 | 2.6803 | 1.1 |
| 34.547 | 2.5942 | 1.7 |
| 34.796 | 2.5761 | 2.4 |
| 35.295 | 2.5408 | 6.8 |
| 35.693 | 2.5134 | 6.4 |

Example 8

Example 1 was repeated, except that n-tetrabutyl titanate was added into the system as a titanium source to replace a part of the germanium source, with a replacement ratio of 2%.

The XRD spectrum data of the product (in a calcined form) was shown in Table 8, and the XRD spectrum was similar to that of FIG. 1.

The obtained product molecular sieve had a specific surface area of 218 m$^2$/g, and a micropore volume of 0.08 cm$^3$/g.

The product molecular sieve was measured by inductively coupled plasma atomic emission spectroscopy (ICP) to have a $SiO_2/GeO_2$=3.8 and a $SiO_2/TiO_2$=133.5.

TABLE 8

| 2θ/° | d/Å | I/I$_0$ × 100 |
|---|---|---|
| 6.617 | 13.3473 | 32.5 |
| 8.333 | 10.6023 | 100 |
| 10.325 | 8.5605 | 2.9 |
| 11.724 | 7.5418 | 0.6 |
| 13.303 | 6.6502 | 6 |
| 13.561 | 6.5241 | 8.9 |
| 14.424 | 6.1357 | 0.9 |
| 15.652 | 5.6569 | 14.3 |
| 16.117 | 5.4946 | 1.1 |
| 17.978 | 4.9299 | 6.7 |
| 19.991 | 4.4378 | 4.5 |
| 20.762 | 4.2747 | 8.3 |
| 21.628 | 4.1055 | 74 |
| 23.266 | 3.82 | 3.5 |
| 23.918 | 3.7174 | 3.9 |
| 24.529 | 3.6262 | 3.6 |
| 25.258 | 3.5231 | 14 |
| 25.811 | 3.4489 | 8.4 |
| 26.225 | 3.3953 | 6.3 |
| 27.292 | 3.265 | 1.8 |
| 27.921 | 3.1928 | 0.9 |
| 28.691 | 3.1089 | 2.5 |
| 29.005 | 3.0759 | 5.2 |
| 30.013 | 2.9749 | 3.2 |
| 31.137 | 2.87 | 1 |
| 31.41 | 2.8456 | 2.4 |
| 31.666 | 2.8233 | 1.7 |
| 32.204 | 2.7773 | 3 |
| 32.894 | 2.7206 | 1.5 |
| 33.682 | 2.6588 | 0.6 |
| 35.065 | 2.557 | 1.9 |
| 35.753 | 2.5093 | 6.7 |
| 38.48 | 2.3375 | 0.7 |
| 39.796 | 2.2632 | 1.3 |

Example 9

The product molecular sieve obtained in example 1 and 0.7 wt % Al(NO)$_3$ solution were loaded into a three-neck flask at a weight ratio of molecular sieve:Al(NO$_3$)$_3$ solution=1:50. Reaction was conducted for 6 hours in an oil bath at 80° C. under stirring. The solid sample was centrifuged and washed after reaction, and was put into an oven at 100° C. for overnight drying. The dried sample was then reacted with an 0.01 mol/L of HCl solution at a weight ratio of molecular sieve:HCl solution=1:50 at room temperature for 6 hours under stirring. The solid sample was centrifuged and washed after the reaction, and was dried in an oven at 100° C. overnight to obtain a powder. The product was measured by inductively coupled plasma atomic emission spectroscopy (ICP) to have a $SiO_2/GeO_2$=4.2 and a $SiO_2/Al_2O_3$=102.3.

Example 10

3 g of the powder sample prepared in example 9 was mixed with 2 g of alumina and 0.3 g of sesbania powder, kneaded with 5 wt % of nitric acid, extruded into a rod of φ1.6*2 mm, and then dried at 110° C. and calcined at 550° C. for 6 hours in an air atmosphere, to prepare a desired molecular sieve composition. The molecular sieve composition could be used as an adsorbent or a catalyst.

Example 11

The molecular sieve composition prepared in the example 10 was crushed and sieved. 20 mg particles having a particle size of 20-40 meshes was loaded into a pulse fixed bed reactor, activated for 1 h in a nitrogen atmosphere at 300° C., and cooled to the reaction temperature of 250° C. A pulse sample injection mode was adopted to inject 0.4 microliter of cumene into the reactor instantly at one time. The cumene was subjected to a cracking reaction through a molecular sieve composition bed layer. The mixture after the reaction was directly fed into a gas chromatography for analysis. The conversion rate of the cumene was 96.4%, and main products were propylene and benzene.

The invention claimed is:

1. A molecular sieve SCM-14 having an X-ray diffraction pattern substantially as shown in Table A-1 or Table A-2 below,

TABLE A-1

| 2θ (°)[a] | d-distance (Å)[b] | Relative intensity (I/I$_0$ × 100) |
|---|---|---|
| 6.632 | 13.317 | s-vs |
| 8.384 | 10.537 | s-vs |
| 15.587 | 5.680 | w-m |
| 20.661 | 4.295 | w |
| 21.692 | 4.094 | w-vs |
| 25.693 | 3.464 | w-m |

[a]= ±0.3°,
[b]is a function of 2θ,

TABLE A-2

| 2θ (°)[a] | d-distance (Å) | Relative intensity (I/I$_0$ × 100) |
|---|---|---|
| 6.632 | 13.344 ± 0.603 | s-vs |
| 8.384 | 10.551 ± 0.377 | s-vs |
| 15.587 | 5.682 ± 0.109 | w-m |
| 20.661 | 4.296 ± 0.062 | w |
| 21.692 | 4.094 ± 0.056 | w-vs |
| 25.693 | 3.465 ± 0.040 | w-m |

[a]= ±0.3°.

wherein the as-synthesized molecular sieve, before being subject to calcination, has a schematic chemical composition of the formula "kF.mQ.SiO$_2$.1/nGeO$_2$.pH$_2$O", wherein, the molar ratio of silicon to germanium is n, n≤30, 0.01≤k≤0.6, Q is an organic template, and 0.01≤m≤0.6, wherein the organic template is 4-pyrrolidinyl pyridine, a quaternary ammonium form of formula (A-1), a quaternary ammonium form of formula (A-2), or a quaternary ammonium form of formula (A-3),

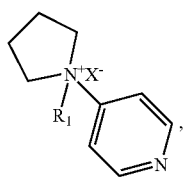
(A-1)

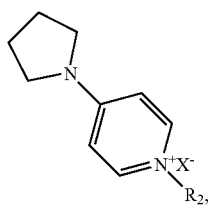
(A-2)

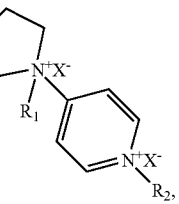
(A-3)

wherein R$_1$ and R$_2$ are each independently H or C$_{1-8}$ alkyl, and X$^-$ is a halogen ion or a hydroxide ion (OH$^-$), and 0.005≤p≤0.5.

2. The molecular sieve SCM-14 according to claim 1, wherein the as-synthesized molecular sieve, before being subject to calcination, has a schematic chemical composition of the formula "kF.mQ.SiO$_2$.1/nGeO$_2$.pH$_2$O", wherein 1≤n≤5, 0.02≤k≤0.2, 0.04≤m≤0.1, and 0.02≤p≤0.2.

3. A process of preparing molecular sieve SCM-14, comprising:

crystallizing a mixture containing a silicon source, a germanium source, a fluorine source, an organic template, and water to obtain the molecular sieve; and optionally calcining the obtained molecular sieve, wherein the organic template is 4-pyrrolidinyl pyridine, a quaternary ammonium form of formula (A-1), a quaternary ammonium form of formula (A-2), or a quaternary ammonium form of formula (A-3),

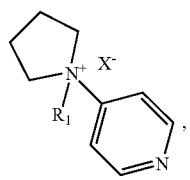
(A-1)

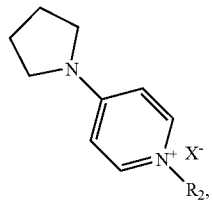
(A-2)

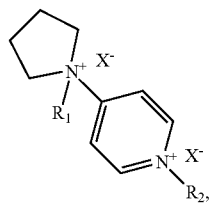
(A-3)

wherein R$_1$ and R$_2$ are each independently H or C$_{1-8}$ alkyl, and X$^-$ is a halogen ion or a hydroxide ion (OH$^-$).

4. The process of preparing molecular sieve SCM-14 according to claim 3, wherein the silicon source is at least one selected from the group consisting of silicic acid, silica gel, silica sol, tetraalkyl orthosilicate and water glass; the germanium source is at least one selected from the group consisting of germanium oxide, germanium nitrate and tetraalkoxygermanium; and a molar ratio of the silicon source (calculated as SiO$_2$), the germanium source (calculated as GeO$_2$), the fluorine source (calculated as F), the organic template agent and water is 1:(0.05-2): (0.1-0.8): (0.1-0.8): (10-40).

5. The process according to claim 4, wherein the molar ratio of the silicon source (calculated as $SiO_2$), the germanium source (calculated as $GeO_2$), the fluorine source (calculated as F), the organic template agent and water is 1:(0.2-1): (0.3-0.5): (0.3-0.5): (15-20).

6. The process of preparing molecular sieve SCM-14 according to claim 3, wherein the crystallization step further comprises: firstly, crystallizing at 91-130° C. for 8 hours to 3 days, and then crystallizing at 140-210° C. for 1-15 days.

7. The process according to claim 6, wherein the crystallization step comprises firstly crystallizing at 100-120° C. for 12 to 36 hours and then crystallizing at 160-180° C. for 2 to 7 days.

8. The process of preparing molecular sieve SCM-14 according to claim 3, further comprising: prior to crystallization, ageing the mixture at an ageing temperature of 50-90° C. for an ageing duration of 30 minutes to 2 days.

9. The process of preparing molecular sieve SCM-14 according to claim 3, wherein the mixture further comprises a source of an element other than silicon and germanium, wherein the source of element other than silicon and germanium is at least one selected from the group consisting of boron, aluminum, tin, zirconium and titanium, and the molar ratio of the oxide source (calculated as the corresponding oxide) to the germanium source (calculated as $GeO_2$) is (0.01-0.1):1.

10. The process according to claim 3, wherein the mixture further comprises at least one oxide source selected from the group consisting of a boron oxide source, an alumina source, a tin oxide source, a zirconium oxide source, and a titanium oxide source; and a molar ratio of the oxide source (calculated as the corresponding oxide) to the germanium source (calculated as $GeO_2$) is (0.02-0.08):1.

11. A molecular sieve SCM-14 having an X-ray diffraction pattern as shown in FIG. 1.

12. A molecular sieve SCM-14 having an X-ray diffraction pattern substantially as shown in table below:

| $2\theta$ (°) | d-distance (Å) | $I/I_0 \times 100$ |
|---|---|---|
| 6.576 | 13.4293 | 46.8 |
| 8.278 | 10.6724 | 100 |
| 9.956 | 8.8774 | 1.4 |
| 10.27 | 8.6066 | 4.8 |
| 11.639 | 7.5965 | 1 |
| 13.192 | 6.7058 | 6.5 |
| 13.465 | 6.5702 | 9.4 |
| 14.287 | 6.1943 | 1.3 |
| 15.549 | 5.6943 | 21.6 |
| 15.996 | 5.536 | 1.8 |
| 16.61 | 5.3327 | 0.5 |
| 17.848 | 4.9657 | 8.1 |
| 19.848 | 4.4696 | 7 |
| 20.636 | 4.3006 | 9.4 |
| 21.458 | 4.1376 | 86.5 |
| 22.272 | 3.9883 | 5.2 |
| 23.101 | 3.8469 | 5.2 |
| 23.417 | 3.7958 | 1.6 |
| 23.765 | 3.7409 | 6.4 |
| 24.355 | 3.6516 | 6.1 |
| 25.06 | 3.5504 | 17.8 |
| 25.633 | 3.4724 | 14.5 |
| 26.04 | 3.4191 | 7.3 |
| 27.027 | 3.2964 | 2 |
| 27.734 | 3.214 | 1.2 |
| 28.488 | 3.1305 | 4.2 |
| 28.779 | 3.0996 | 8.3 |
| 29.152 | 3.0608 | 0.9 |
| 29.791 | 2.9965 | 4.1 |
| 30.904 | 2.8911 | 1.2 |
| 31.178 | 2.8664 | 3.7 |
| 31.418 | 2.8449 | 2.9 |
| 31.999 | 2.7946 | 4.3 |
| 32.68 | 2.738 | 1.9 |
| 33.403 | 2.6803 | 1.1 |
| 34.547 | 2.5942 | 1.7 |
| 34.796 | 2.5761 | 2.4 |
| 35.328 | 2.5386 | 7.3 |
| 36.141 | 2.4833 | 2.6 |
| 37.503 | 2.3962 | 0.8 |
| 38.232 | 2.3521 | 1.2 |
| 39.461 | 2.2816 | 1.7 |
| 40.331 | 2.2344 | 1.5 |
| 41.371 | 2.1806 | 2.6 |
| 41.603 | 2.169 | 2.7 |
| 42.391 | 2.1305 | 1.4 |
| 43.005 | 2.1015 | 0.9 |
| 44.101 | 2.0518 | 1.9 |
| 44.608 | 2.0296 | 1.1. |

13. A molecular sieve SCM 14 having an X-ray diffraction pattern substantially as shown in table below:

| $2\theta$ (°) | d-distance (Å) | $I/I_0 \times 100$ |
|---|---|---|
| 6.651 | 13.278 | 100 |
| 8.273 | 10.6793 | 47.9 |
| 10.049 | 8.7952 | 8.7 |
| 10.378 | 8.5166 | 10.1 |
| 13.535 | 6.5364 | 9.2 |
| 14.398 | 6.147 | 0.4 |
| 15.67 | 5.6505 | 23.5 |
| 18.01 | 4.9213 | 9.2 |
| 20.008 | 4.4342 | 11.4 |
| 20.832 | 4.2605 | 10.2 |
| 21.662 | 4.0991 | 33.9 |
| 22.472 | 3.9532 | 6.5 |
| 23.477 | 3.786 | 0.5 |
| 23.789 | 3.737 | 0.4 |
| 24.006 | 3.7039 | 8.6 |
| 24.421 | 3.642 | 0.5 |
| 25.09 | 3.5462 | 8.1 |
| 25.628 | 3.473 | 14.4 |
| 26.218 | 3.3963 | 4.4 |
| 28.743 | 3.1033 | 6.3 |
| 29.039 | 3.0724 | 12.1 |
| 31.477 | 2.8398 | 3.7 |
| 35.624 | 2.5181 | 8.4 |
| 46.985 | 1.9323 | 4.2. |

14. A molecular sieve SCM-14 having an X-ray diffraction pattern substantially as shown in table below:

| $2\theta$ (°) | d-distance (Å) | $I/I_0 \times 100$ |
|---|---|---|
| 6.56 | 13.4633 | 88.7 |
| 8.336 | 10.5982 | 100 |
| 10.17 | 8.6909 | 5.1 |
| 11.582 | 7.6338 | 3.7 |
| 13.166 | 6.7188 | 9.3 |
| 14.288 | 6.1936 | 2.8 |
| 15.449 | 5.7309 | 39.5 |
| 15.855 | 5.5849 | 3.5 |
| 16.736 | 5.2928 | 2.1 |
| 17.574 | 5.0424 | 2.2 |
| 17.864 | 4.9613 | 4 |
| 19.814 | 4.477 | 5.1 |
| 20.43 | 4.3435 | 12.6 |
| 21.599 | 4.1109 | 91.8 |
| 23.02 | 3.8604 | 6.3 |
| 23.318 | 3.8116 | 4.3 |

-continued

| 2θ (°) | d-distance (Å) | I/I₀ × 100 |
|---|---|---|
| 23.567 | 3.772 | 7.5 |
| 24.263 | 3.6653 | 5.7 |
| 24.82 | 3.5843 | 6.8 |
| 25.243 | 3.5251 | 12.8 |
| 25.516 | 3.488 | 25.3 |
| 26.056 | 3.4169 | 10.1 |
| 26.87 | 3.3153 | 2.7 |
| 27.3 | 3.264 | 1.5 |
| 27.858 | 3.2 | 1.2 |
| 28.323 | 3.1484 | 5.5 |
| 28.571 | 3.1216 | 10.4 |
| 29.054 | 3.0709 | 1.6 |
| 29.974 | 2.9787 | 4.1 |
| 30.837 | 2.8972 | 4.5 |
| 31.219 | 2.8626 | 3.4 |
| 32.024 | 2.7925 | 6.4 |
| 32.323 | 2.7674 | 2.6 |
| 32.726 | 2.7342 | 0.7 |
| 33.071 | 2.7064 | 0.8 |
| 33.376 | 2.6824 | 1.5 |
| 34.806 | 2.5754 | 1.3. |

15. A molecular sieve SCM-14 having an X-ray diffraction pattern substantially as shown in table below:

| 2θ (°) | d-distance (Å) | I/I₀ × 100 |
|---|---|---|
| 6.576 | 13.4293 | 46.8 |
| 8.278 | 10.6724 | 100.0 |
| 9.956 | 8.8774 | 1.4 |
| 10.270 | 8.6066 | 4.8 |
| 11.639 | 7.5965 | 1.0 |
| 13.216 | 6.6936 | 6.9 |
| 13.465 | 6.5702 | 9.4 |
| 14.287 | 6.1943 | 1.3 |
| 15.549 | 5.6943 | 21.6 |
| 15.996 | 5.5360 | 1.8 |
| 16.643 | 5.3224 | 0.5 |
| 17.657 | 5.0189 | 4.1 |
| 17.848 | 4.9657 | 8.1 |
| 19.848 | 4.4696 | 7.0 |
| 20.636 | 4.3006 | 9.4 |
| 21.458 | 4.1376 | 86.5 |
| 22.272 | 3.9883 | 5.2 |
| 23.101 | 3.8469 | 5.2 |
| 23.417 | 3.7958 | 1.6 |
| 23.765 | 3.7409 | 6.4 |
| 24.355 | 3.6516 | 6.1 |
| 24.886 | 3.5749 | 9.5 |
| 25.060 | 3.5504 | 17.8 |
| 25.633 | 3.4724 | 14.5 |
| 26.040 | 3.4191 | 7.3 |
| 26.986 | 3.3013 | 2.4 |
| 27.734 | 3.2140 | 1.2 |
| 28.488 | 3.1305 | 4.2 |
| 28.779 | 3.0996 | 8.3 |

-continued

| 2θ (°) | d-distance (Å) | I/I₀ × 100 |
|---|---|---|
| 29.152 | 3.0608 | 0.9 |
| 29.791 | 2.9965 | 4.1 |
| 30.904 | 2.8911 | 1.2 |
| 31.178 | 2.8664 | 3.7 |
| 31.418 | 2.8449 | 2.9 |
| 31.999 | 2.7946 | 4.3 |
| 32.299 | 2.7694 | 1.7 |
| 32.680 | 2.7380 | 1.9 |
| 33.403 | 2.6803 | 1.1 |
| 34.547 | 2.5942 | 1.7 |
| 34.796 | 2.5761 | 2.4 |
| 35.295 | 2.5408 | 6.8 |
| 35.693 | 2.5134 | 6.4. |

16. A molecular sieve SCM-14 having an X-ray diffraction pattern substantially as shown in table below:

| 2θ (°) | d-distance (Å) | I/I₀ × 100 |
|---|---|---|
| 6.617 | 13.3473 | 32.5 |
| 8.333 | 10.6023 | 100 |
| 10.325 | 8.5605 | 2.9 |
| 11.724 | 7.5418 | 0.6 |
| 13.303 | 6.6502 | 6 |
| 13.561 | 6.5241 | 8.9 |
| 14.424 | 6.1357 | 0.9 |
| 15.652 | 5.6569 | 14.3 |
| 16.117 | 5.4946 | 1.1 |
| 17.978 | 4.9299 | 6.7 |
| 19.991 | 4.4378 | 4.5 |
| 20.762 | 4.2747 | 8.3 |
| 21.628 | 4.1055 | 74 |
| 23.266 | 3.82 | 3.5 |
| 23.918 | 3.7174 | 3.9 |
| 24.529 | 3.6262 | 3.6 |
| 25.258 | 3.5231 | 14 |
| 25.811 | 3.4489 | 8.4 |
| 26.225 | 3.3953 | 6.3 |
| 27.292 | 3.265 | 1.8 |
| 27.921 | 3.1928 | 0.9 |
| 28.691 | 3.1089 | 2.5 |
| 29.005 | 3.0759 | 5.2 |
| 30.013 | 2.9749 | 3.2 |
| 31.137 | 2.87 | 1 |
| 31.41 | 2.8456 | 2.4 |
| 31.666 | 2.8233 | 1.7 |
| 32.204 | 2.7773 | 3 |
| 32.894 | 2.7206 | 1.5 |
| 33.682 | 2.6588 | 0.6 |
| 35.065 | 2.557 | 1.9 |
| 35.753 | 2.5093 | 6.7 |
| 38.48 | 2.3375 | 0.7 |
| 39.796 | 2.2632 | 1.3. |

* * * * *